(12) United States Patent
Zimmeck

(10) Patent No.: US 9,750,763 B2
(45) Date of Patent: *Sep. 5, 2017

(54) SOLUTION FOR PERITONEAL DIALYSIS

(71) Applicant: Fresenius Medical Care Deutschland GmbH, Bad Homburg (DE)

(72) Inventor: Thomas Zimmeck, Hohenlockstedt (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 10 days.

This patent is subject to a terminal disclaimer.

(21) Appl. No.: 14/534,298

(22) Filed: Nov. 6, 2014

(65) Prior Publication Data

US 2015/0150905 A1     Jun. 4, 2015

Related U.S. Application Data

(63) Continuation of application No. 12/073,207, filed on Mar. 3, 2008, now Pat. No. 8,883,762, which is a continuation of application No. 10/418,201, filed on Apr. 18, 2003, now Pat. No. 7,345,029.

(30) Foreign Application Priority Data

Apr. 18, 2002  (DE) .................. 102 17 356

(51) Int. Cl.

| | |
|---|---|
| *A61K 31/715* | (2006.01) |
| *A61K 33/00* | (2006.01) |
| *A61K 33/06* | (2006.01) |
| *A61K 33/10* | (2006.01) |
| *A61K 33/14* | (2006.01) |
| *A61M 1/16* | (2006.01) |
| *A61M 1/28* | (2006.01) |
| *A61K 31/718* | (2006.01) |

(52) U.S. Cl.
CPC ............ *A61K 33/14* (2013.01); *A61K 31/715* (2013.01); *A61K 31/718* (2013.01); *A61K 33/00* (2013.01); *A61K 33/06* (2013.01); *A61K 33/10* (2013.01); *A61M 1/1668* (2014.02); *A61M 1/287* (2013.01)

(58) Field of Classification Search
CPC .... A61K 31/715; A61K 31/718; A61K 33/06; A61K 33/10; A61K 33/14; A61M 1/287; A61M 1/1668
See application file for complete search history.

(56) References Cited

U.S. PATENT DOCUMENTS

| | | |
|---|---|---|
| 4,182,756 A | 1/1980 | Ramsay et al. |
| 5,382,437 A | 1/1995 | Ecanow |
| 5,580,941 A | 12/1996 | Krause et al. |
| 5,738,897 A | 4/1998 | Gidley et al. |
| 5,827,820 A | 10/1998 | duMoulin et al. |
| 6,193,956 B1 | 2/2001 | Liu et al. |
| 6,277,815 B1 | 8/2001 | Knerr |
| 6,284,140 B1 | 9/2001 | Sommermeyer et al. |
| 6,306,836 B1 | 10/2001 | Martis et al. |
| 6,582,734 B1 | 6/2003 | Wei et al. |
| 7,345,029 B2 | 3/2008 | Zimmeck |
| 2001/0031282 A1 | 10/2001 | Peter et al. |
| 2002/0086059 A1 | 7/2002 | Bausch et al. |

FOREIGN PATENT DOCUMENTS

| | | |
|---|---|---|
| AU | 52022/93 | 6/1994 |
| DE | 4242926 | 6/1994 |
| DE | 19748290 | 5/1999 |
| DE | 69230473 | 5/2000 |
| DE | 19912850 | 9/2000 |
| EP | 0170275 | 7/1985 |
| EP | 0564672 | 4/1992 |
| EP | 0602585 | 12/1993 |
| EP | 0668785 | 12/1999 |
| EP | 1008341 | 6/2000 |
| JP | 08131542 | 5/1996 |
| WO | WO 83/00087 | 1/1983 |
| WO | WO 02/081005 | 10/2002 |

*Primary Examiner* — John Pak
(74) *Attorney, Agent, or Firm* — Jacobson Holman, PLLC.

(57) ABSTRACT

The present invention relates to a solution for peritoneal dialysis, consisting of at least two single solutions which are combined after a heat sterilization and are administered to a patient, the first single solution containing an osmotic and the second single solution containing a buffer, and one of these single solutions or another single solution containing electrolyte salts. The avoidance of a glucose-like degradation as well as hydrolysis during sterilization and storage while maintaining a neutral mixture pH is achieved according to the invention by the osmotic comprising a glucose polymer and/or glucose polymer derivative, and the pH of the first single solution being between 3.5 and 5.0. The present invention further relates to a twin-chambered pouch consisting of a plastic pouch with at least one first chamber and a second chamber, the first single solution being included in the first chamber and the second single solution being included in the second chamber.

15 Claims, 1 Drawing Sheet

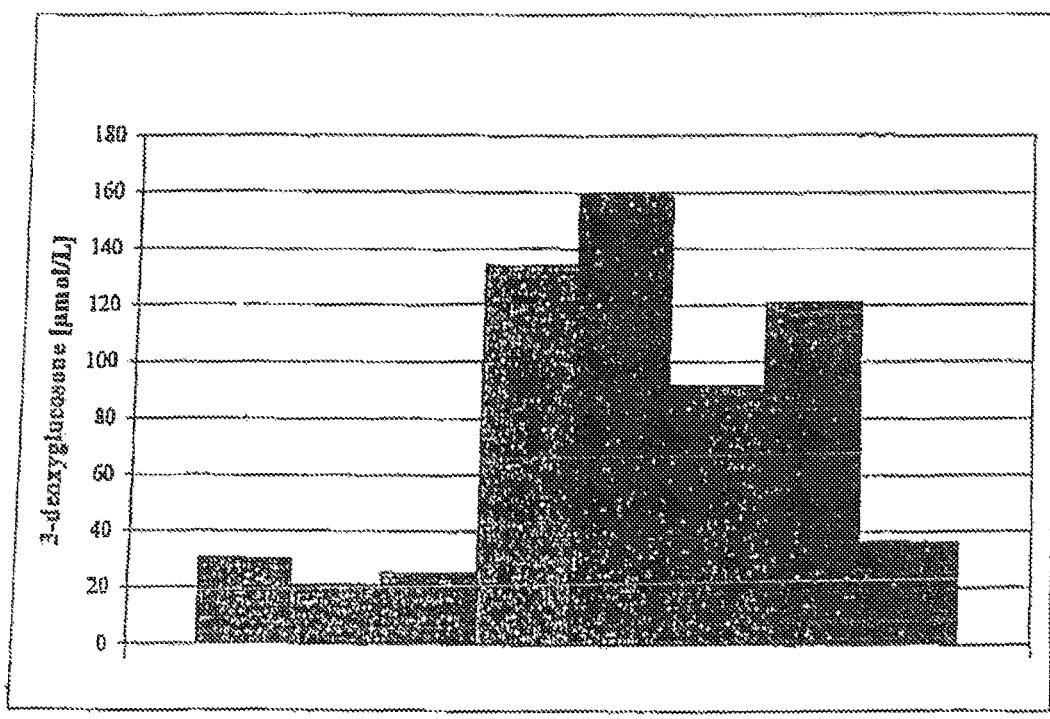

SOLUTION FOR PERITONEAL DIALYSIS

This is a continuation of Ser. No. 12/073,207, filed Mar. 3, 2008, now U.S. Pat. No. 8,883,762, which is a continuation of Ser. No. 10/418,201, filed Apr. 18, 2003, now U.S. Pat. No. 7,345,023, and which has priority of DE 102 17 356.7 filed Apr. 18, 2002, the disclosures of which are incorporated herein by reference.

The present invention relates to a solution for peritoneal dialysis, consisting of at least two single solutions, which are combined after a heat sterilization and are administered to the patient, the first single solution containing an osmotic and the second single solution containing a buffer, and one of these single solutions or a further single solution containing electrolyte salts.

Solutions for peritoneal dialysis usually contain three components: the buffer system, electrolytes and an osmotic. Often glucose is used as an osmotic essentially serving to decrease the water content of the blood in an osmotically active concentration, since it has a good osmolarity and is tolerated well. A further advantage of the use of glucose is the cost advantage compared to other possible osmotics.

A disadvantage of the use of glucose, however, is that it caramelizes or isomerizes during heat sterilization, or degradation products are formed which develop harmful effects in the patient's body, e.g. further react with proteins, which is not desired. In order to prevent these disadvantages it is known from DE 197 48 290 A1 to use a peritoneal dialysis solution consisting of two single solutions, the pH of the single solution that contains the glucose and electrolyte salts being adjusted to a value below 3.2. Furthermore it is disclosed to provide the salt of a weak acid with pKa<5 in a second alkaline single solution apart from the bicarbonate present in a low concentration, in order to obtain a phsiologically tolerable pH in the mixture of the single solutions. These two single solutions are mixed with each other after heat sterilization, and the mixture is then administered to the patient. If pH values below 3.2 are used, the degradation of glucose can be largely prevented.

Apart from the mentioned use of glucose as an osmotic, it is known for example from WO 83/00087 to use glucose polymers as a substitute for or in addition to glucose. Glucose polymers are used especially for long dwelling times in peritoneal dialysis solutions due to their advantageous ultrafiltration profile. Due to the slow diffusion of glucose polymers relative to glucose, the osmolarity is essentially maintained throughout the treatment. Furthermore, the glucose load of the patient is reduced which is especially advantageous in case of diabetic patients.

The degradation at almost neutral pH values which is observed using glucose, especially in presence of lactate, and the conversion, e.g. to fructose, acetaldehyde and 3-desoxyglucosone is somewhat true for glucose polymers and glucose polymer derivatives as well. For this reason, glucose polymer- or glucose polymer derivatives-containing solutions cannot be sterilized at neutral pH values.

FIG. 1 shows the concentration of the degradation product 3-desoxyglucosone for various single solutions containing the osmotic and being present in twin-chambered pouches, the solution shown at the right containing a glucose polymer as an osmotic instead of glucose. From this it can be seen that relatively large amounts of degradation products are found even when glucose polymers are used. This is due to the fact that not only the terminal carbonyl moiety of glucose polymers is converted but also can a glucose unit be cleaved off from the polymer. Furthermore it is possible that so far unknown conversion products are formed which are still contained within the polymer compound of the osmotic.

In the already mentioned WO 83/00087 peritoneal dialysis solutions are described in which glucose polymers with a degree of polymerization of at least 4 are used as osmotic. The peritoneal dialysis solution of this publication has a pH in the range of 5 to 7.4, which during heat sterilization may be associated with the above mentioned disadvantages.

If the problems related to the degradation or the conversion of glucose polymers or their derivatives during storage and heat sterilization are to be avoided by adjusting the pH of values below 3.2, as it is known for glucose from DE 197 48 290 A1, the problem arises that the polymers are hydrolized, which results in breaking of the polymer chain or in decrease of the average molecular weight. The preparation of solutions containing glucose polymers or glucose polymer derivatives is aggreviated since they might contain acids which has to be considered when the pH is adjusted.

SUMMARY OF THE INVENTION

It is therefore an object of the present invention to provide a peritoneal dialysis solution containing glucose polymers and/or glucose polymer derivatives which are not subjected to glucose-like degradation during storage and heat sterilization, and the mixture of which having a pH value in the neutral range.

BRIEF DESCRIPTION OF THE DRAWINGS

FIG. 1 is a graph showing the concentration of the degradation product 3-desoxyglucosone for various single solutions.

DETAILED DESCRIPTION AND PREFERRED EMBODIMENTS

According to the invention, the glucose degradation problem is solved by the osmotic comprising a glucose polymer and/or a glucose polymer derivative, and the pH value of the first single solution being in the range of 3.0 to 5.0. It is especially advantageous that the pH is in the range between 4.0 and 4.3, preferably at 4.2. With these pH values essentially no polymer degradation is observed. This is especially true for a pH of 4.0. The addition of 0.2 pH units to the preferred value of 4.2 is intended as a safety measure for the possible generation of acids during sterilisation and storage. In the invention pH range, no hydrolysis of the osmotic nor a glucose-like degradation takes place in noticeable extend. The osmotic can be formed exclusively with the glucose polymer and/or the glucose polymer derivative. It is also conceivable that further osmotically active substances are present.

In a further embodiment of the present invention it is envisioned that the glucose polymer derivative is hydroxyethyl starch (HES). The present invention also refers to other derivatized glucose polymers, in which preferably not the free carbonyl group of the molecules has been modified during derivatization.

The first single solution may contain the osmotic, calcium ions, magnesium ions, sodium ions, $H^+$ excess ions and chloride ions.

In a preferred embodiment of the present invention, the buffer contains bicarbonate. This is a very tolerable buffer system being in equilibrium with carbonate in the alkaline range and with $CO_2$ in the acidic range. Apart from or in addition to bicarbonate, other buffer system are conceivable as well, that buffer in a physiological pH of approx. 7. Hereby, preferably substances are to be named which may be degraded easily to bicarbonate in the body. For example, lactate or pyruvate may be considered. Apart from bicarbonate or other puffer systems, the second single solution further contains mainly sodium ions.

It is advantageous that the bicarbonate concentration is adjusted according to the acidity of the first single solution, and is determined according to the formula: bicarbonate concentration [mmol/L]=5×acidity of the first single solution [mmol/L]×$V_A$÷$V_B$, with $V_A$ being the volume of the first single solution and $V_B$ being the volume of the second single solution.

At an acidity of 0.2 mmol/L, the optimal bicarbonate concentration is 0.5 to 2.0 mmol/L when the compartments of a twin-chambered pouch are equally sized. Accordingly, the bicarbonate concentration can be in a range the lower limit of which is determined by half of the biocarbonate concentration determined according to the previous paragraph, and the upper limit of which is determined by twice the biocarbonate concentration determined according to the previous paragraph.

In a further embodiment of the present invention it is envisioned that the buffer contains the salt of a weak acid, preferably lactate. The pKa of the weak acid may be <5. It may be envisioned that the buffer contains a mixture e.g. of bicarbonate and the salt of a weak acid, e.g. lactate. If the bicarbonate content is kept low, e.g. ≤10 mmol/L, as it is suggested in DE 197 48 290 A1, it has the advantage that the $CO_2$ pressure within the storage pouch is low so that no special provisions have to be made with respect to the pouch foil. A conventional polyolefin foil may be used as a $CO_2$ barrier.

The first single solution may contain a physiologically tolerable acid, especially hydrochloric acid. With this, the desired pH range of the first single solution can be adjusted without problems.

Apart from the osmotic, the first single solution may contain the following components:
sodium ions [mmol/L]: 180-200
calcium ions [mmol/L]: 2-4
magnesium ions [mmol/L]: 0.8-1.2
$H^+$ excess [mmol/L]: 0.05-0.1
chloride ions [mmol/L]: 197-210

In a further embodiment of the present invention it is envisioned that the bicarbonate concentration of the second single solution is in the range between 0.5 and 2.0 mmol/L, preferably 1.0 mmol/L.

It is especially advantageous that the first and second single solutions are storable individually in a twin-chambered pouch. The use of a twin-chambered pouch results in a very convenient handling of the solution, i.e. a reliable separation of the two single solutions during storage, and fast mixing when desired. The separation of the single solutions is reasonable in order to prevent, that unsoluble precipitations are formed using bicarbonate as buffer together with calcium. Furthermore, the reaction of the glucose polymers or their derivatives with lactate as a buffer system can be avoided by the separation.

In addition, the present invention relates to a twin-chambered pouch for a solution according to the instant invention, consisting of a plastic pouch with at least one first chamber and one second chamber, the first single solution being included in the first chamber and the second single solution being included in the second chamber. Favourably, means are envisioned by which the two chambers are separated from each other and the activation of which enables the mixing of the content of both chambers. Hereby, the first and second chamber may be arranged adjacently. Preferably, a weld is provided which separates the chambers and opens in case of pressing onto one of the chambers. If dimensioned accordingly, the weld opens in case of pressing onto one of the fluid-filled chambers so that the contents of both chambers may be mixed and the mixture be finally administered to the patient.

In the following, an example for the preparation of the solution according to the invention is provided:

For preparation of the first single solution, sodium chloride, calcium chloride, magnesium chloride as well as a glucose polymer and hydrochloric acid are dissolved in water under stirring. The amount of the added hydrochloric acid is adjusted so that the pH is in the range between 4.1 to 4.3, preferably 4.2. Whereas a pH of 4.0 is to be regarded as ideal since no polymer degradation is observed, the 0.2 pH units to a ph of 4.2 serve as an addition to account for the possible formation of acids during sterilization and storage.

The acidity of this first single solution may be determined by titration with 0.1N NaOH to pH 7.0.

For the second single solution, sodium hydrogen carbonate is dissolved in water under slow stirring. The bicarbonate concentration is determined according to the formula:

$$\text{bicarbonate concentration [mmol/L]}=5\times\text{acidity of the first single solution [mmol/L]}\times V_A \div V_B,$$

with $V_A$ being the volume of the first single solution and $V_B$ being the volume of the second single solution.

Deviations from this calculated bicarbonate concentration by 50% down and by 100% up are possible. If the acidity of the first single solution is e.g. 0.2 mmol/L, and if two equally sized compartments of a twin-chambered pouch are used, the optimal bicarbonate concentration is between 0.5 and 2.0 mmol/L.

The single solutions prepared in this way are then filtered through a membrane sterile filter in a cooling tank. After preparation control and release of the solution, they are filled into a multi-layered foil pouch with two chambers, the first single solution being filled into the first chamber and the second single solution being filled into the second chamber. Both chambers are separated from each other by a weld. The compartments are each closed with a connector. Then, the twin-chambered pouch is packed into an outer pouch, and heat-sterilized at 121° C. After heat sterilization, the weld is opened at least in part by pressing onto one of the chambers resulting in a mixing of the solutions, and by which a mixture pH in the range between 6.8 and 7.0, preferably 6.8, is obtained.

The invention claimed is:

1. A multi-part solution, for peritoneal dialysis designed to be mixed prior to infusion, comprising at least a first single solution and a second single solution, the first single solution containing an osmotic, sodium ions, and chloride ions, and the second single solution containing a buffer and not containing the osmotic, wherein (1) the osmotic comprises at least one of a glucose polymer and a glucose polymer derivative, (2) the first single solution has a pH in the range between 4.0 and 5.0, (3) the buffer contains lactate, (4) bicarbonate ions and calcium ions are not present together in any solution prior to mixing, and (5) lactate and glucose polymer or lactate and glucose polymer derivative are not present together in any solution prior to mixing.

2. The multi-part solution according to claim 1, wherein the osmotic comprises a glucose polymer derivative having at least one modified functional group.

3. The multi-part solution according to claim 2, wherein a free carbonyl group of the glucose polymer derivative is not modified.

4. The multi-part solution according to claim 1, wherein the osmotic exclusively contains the glucose polymer derivative.

5. The multi-part solution according to claim 1, wherein the pH of the first single solution is in the range between 4.0 and 4.3.

6. The multi-part solution according to claim 4, wherein the pH of the first single solution is 4.2.

7. The multi-part solution according to claim 1, wherein the buffer contains a weak acid salt.

8. The multi-part solution according to claim 1, wherein the first single solution contains, in addition to the osmotic, the following components:
   sodium ions [mmol/L]: 180-200;
   calcium ions [mmol/L]: 2-4;
   magnesium ions [mmol/L]: 0.8-1.2;
   chloride ions [mmol/L]: 197-210.

9. The multi-part solution according to claim 1, wherein the first and second single solutions are stored separately in a multi-chambered pouch.

10. A multi-part solution for peritoneal dialysis designed to be mixed prior to infusion, comprising at least a first single solution and a second single solution, the first single solution containing an osmotic and the second single solution containing a buffer and not containing the osmotic, and one of the first single solution, the second single solution, and a third single solution containing electrolyte salts,
   wherein (1) the osmotic comprises a glucose polymer and/or a glucose polymer derivative, (2) the pH of the first single solution is in the range between 4.0 and 5.0, (3) the buffer contains bicarbonate and lactate, (4) bicarbonate ions and calcium ions are not present together in any solution prior to mixing, and (5) lactate and glucose polymer or lactate and glucose polymer derivative are not present together in any solution prior to mixing.

11. The multi-part solution according to claim 10, wherein the bicarbonate concentration is adjusted according to the acidity of the first single solution according to the formula: bicarbonate concentration [mmol/L]=5×acidity of the first single solution [mmol/L]×VA/VB, with VA being the volume of the first single solution and VB being the volume of the second single solution.

12. The multi-part solution according to claim 10, wherein the bicarbonate concentration is between a lower limit determined according to the formula: bicarbonate concentration [mmol/L]=2×acidity of the first single solution [mmol/L]×VA/VB, and an upper limit determined by twice the bicarbonate concentration determined according to the formula: bicarbonate concentration [mmol/L]=10×acidity of the first single solution [mmol/L]×VA/VB, with VA being the volume of the first single solution and VB being the volume of the second single solution.

13. The multi-part solution according to claim 10, wherein the second single solution has a bicarbonate concentration in the range between 0.5 and 2.0 mmol/L.

14. The multi-part solution according to claim 13, wherein the bicarbonate concentration of the second single solution is 1.0 mmol/L.

15. A multi-part solution for peritoneal dialysis designed to be mixed prior to infusion, comprising at least a first and a second single solution, the first single solution containing an osmotic and hydrochloric acid, and the second single solution containing a buffer and not containing the osmotic, and one of the first single solution, the second single solution, and a third single solution containing electrolyte salts,
   wherein (1) the osmotic comprises a glucose polymer and/or a glucose polymer derivative, (2) the pH of the first single solution is in the range between 4.0 and 5.0, (3) the buffer contains lactate, (4) bicarbonate ions and calcium ions are not present together in any solution prior to mixing, and (5) lactate and glucose polymer or lactate and glucose polymer derivative are not present together in any solution prior to mixing.

* * * * *